United States Patent [19]

Piran

[11] Patent Number: 4,814,270

[45] Date of Patent: Mar. 21, 1989

[54] PRODUCTION OF LOADED VESICLES

[75] Inventor: Uri Piran, Norwood, Mass.

[73] Assignee: Becton Dickinson and Company, Franklin Lakes, N.J.

[21] Appl. No.: 650,200

[22] Filed: Sep. 13, 1984

[51] Int. Cl.$^4$ ........................................ G01N 33/544
[52] U.S. Cl. .................................... 435/7; 435/182; 436/528; 436/829; 264/4; 264/4.3; 264/4.6; 514/2
[58] Field of Search .................. 264/4.3, 4.6, 4; 436/829, 535, 528; 428/402.2; 424/38, DIG. 7, 94, 32-37; 514/2; 435/7, 182

[56] References Cited

U.S. PATENT DOCUMENTS

| | | | |
|---|---|---|---|
| 4,123,382 | 10/1978 | Morse et al. | 424/37 X |
| 4,310,506 | 1/1982 | Baldeschweiler et al. | 424/1.1 |
| 4,342,739 | 8/1982 | Kakimi et al. | 436/829 X |
| 4,372,745 | 2/1983 | Mandle et al. | 264/4.3 X |
| 4,483,929 | 11/1984 | Szoka | 436/829 X |
| 4,515,736 | 5/1985 | Deamer | 264/4.3 |
| 4,529,561 | 7/1985 | Hunt et al. | 424/38 X |

FOREIGN PATENT DOCUMENTS 2041517 9/1980 United Kingdom ................ 436/829

OTHER PUBLICATIONS

Olson, et al, "Preparation of Liposomes of Defined Size Distribution by Extrusion Through Polycarbonate Membranes", Biochimica et Biophysica Acta, 557, pp. 9-23 (1979).

Reeves, et al, "Formation and Properties of Thin--Walled Phosphollipid Vesicles", J. Cell. Physiol., vol. 73, pp. 49-60 (1969).

Morris, "Liposomes as a Model System for Investigating Freezing Injury, Effects of Low Temperature on Biological Membranes," pp. 241-262, Acad. Press (1981).

Primary Examiner—Esther M. Kepplinger
Attorney, Agent, or Firm—Elliot M. Olstein; Raymond J. Lillie

[57] ABSTRACT

Vesicles having a material encapsulated therein are produced by placing an "empty" vesicle in a liguid including a material to be encapsulated and perturbing the vesicle, preferable by passage through a porous material.

19 Claims, No Drawings

PRODUCTION OF LOADED VESICLES

This invention relates to the production of vesicles, as well as the use thereof. More particularly the invention relates to vesicles which include encapsulated material, and the use thereof.

Sacs, sometimes referred to as vesicles, as known in the art, can be prepared from a wide variety of materials. Most commonly, such sacs or vesicles, are formed from lipids, in particular phospholipids, and as a result, such sacs are commonly referred to as lipid vesicles or liposomes. The term sac or vesicle includes liposomes.

As known in the art, a vesicle is formed from one or more compounds having both a hydrophobic moiety, and a hydrophilic moiety of sufficient polarity so that the materials produced a vesicle. In one method for producing such vesicles, sometimes referred to as a reverse emulsion technique, as described in U.S. Pat. No. 4,235,871, there is provided a water-in-oil emulsion containing the materials for forming the vesicle (generally phospholipids), as well as the material to be encapsulated in the vesicle, followed by evaporation of the solvent to produce a gel-like mixture, which is converted to a vesicle by either agitation or addition of the gel-like mixture to water. Such a technique produces large sacs which are generally unilamellar, (single wall), or oligolamellar, (generally no more than five walls).

Although such techniques may be employed to produce a vesicle including an encapsulated material problems have been encountered in such production. For example, the material to be encapsulated must be subjected to the same conditions as the material(s) used in forming the vesicle, which may adversely affect the material to be encapsulated. Similarly, the materials used in forming the vesicle may be adversely affected by the materials to be encapsulated.

As a result, there is a need for new procedures for producing vesicles.

In addition, it has been found that many vesicles including encapsulated material and/or which are derivatized (for example, for use in an assay) do not possess the requisite stability. As a result, there is a need for providing improved vesicles.

In accordance with one aspect of the present invention, there is provided a process for producing a sac or vesicle wherein a preformed vesicle, which is essentially free of material to be encapsulated therein, is placed into a liquid containing the material to be encapsulated, followed by introducing at least a portion of the liquid into the vesicle to encapsulate the material in the vesicle.

Applicant has found that by encapsulating (loading) a material into a preformed vesicle, rather than encapsulating the material in the vesicle at the time of producing the vesicle, there can be produced improved vesicles including an encapsulated material.

Applicant has found that improved vesicles containing an encapsulated material can be produced by introducing the material into a preformed sac, without irreparable destroying the integrity of the sac. Although applicant does not intend the present invention to be limited by any explanation, it is believed that the permeability of the vesicles can be temporarily increased by perturbing the vesicles by subjecting the vesicles, for example, to shear stress. Such perturbance can be created by a variety of procedures; for example, changes in osmotic pressure; subjecting the vesicle suspended in a liquid to a pressure drop or a sequential change in pressure; cavitation; the action of a Galleon press, high velocity flow through a tube, passage through a porous material, etc.

The vesicle is temporarily disrupted or perturbed so as to introduce liquid into the preformed vesicle at a temperature which is at least 4° C., and which is preferably at least 20° C. Temperature may have an affect on the efficiency of the encapsulation; accordingly, selection of a specific temperature above 4° C. to maximize efficiency is deemed to be within the skill of the art from the teachings herein.

As should be apparent, from the teachings herein, the conditions employed for introducing liquid into the preformed vesicle are such that the integrity of the vesicle is not permanently destroyed.

In accordance with a preferred procedure of the present invention, a vesicle, which has been preformed, and which is essentially free of the material to be encapsulated, is passed through a porous material in a liquid containing the material to be encapsulated, with such passage through the porous material causing the liquid, which contains the material to be encapsulated, to flow into the vesicle. In such a procedure, an "empty" vesicle (by "empty" it is meant that the interior of the vesicle is essentially free of the material which is be eventually encapsulated into the vesicle) is initially prepared, followed by extruding the "empty" vesicle, in a liquid containing the material to be encapsulated, through an appropriate porous material to incorporate such material into the vesicle.

The porous material is preferably in the form of one or more membranes. As should be apparent, the pore size of the porous material is such that the vesicle is perturbed or disrupted sufficiently to permit the liquid to enter the vesicle, without permanently or irreparably destroying the vesicle; i.e., the vesicle is resealed so that material does not leak therefrom.

The vesicle which is employed as a starting material, and which is "empty" may be either single walled or multilamellar, and may be prepared by a wide variety of procedures, as known in the art.

The "empty" vesicle is suspended in a liquid which will not destroy the vesicle, and which contains the material to be encapsulated. Water is a preferred liquid; however, the liquid may be comprised of a hydrophilic organic material such as glycerol. The liquid contains the material which is to be encapsulated into the "empty" vesicle in a concentration sufficient to provide the desired amount of material in the vesicle. Applicant has surprisingly found that in accordance with the procedure of the present invention, an increase in the concentration of the material to be encapsulated into the preformed vesicle in the liquid in which the vesicle is suspended, does not result necessarily in an increase in the amount of material in the vesicle. As a result, the concentration of material is controlled to provide a desired concentration in the vesicle, and an increase in the concentration of material in the liquid in which the preformed vesicle is suspended does not necessarily increase the concentration of material in the vesicle.

The porous material which is employed in the process of the present invention may be formed from any one of a wide variety of materials which have a pore size such that the vesicle is broken and resealed so that the liquid may enter the vesicle and be encapsulated therein. The pore size is also selected in a manner such that the vesicle, including the encapsulated material, will have the desired size. In general, the pore size is from 0.05 micron to 10 microns, and preferably from 0.1 micron to 5 microns. It is also to be understood that the porous material need not necessarily have a pore size less than the size of the vesicle in order to perturb the vesicle so as to permit introduction of a material to be encapsulated. However, in the preferred embodiments, the pore size is less than the size of the vesicle. It is to be understood, however, that the scope of the invention is not limited by such pore sizes.

The extrusion of the "empty" vesicle through a porous material such as a membrane may be accomplished in one or more steps, and if more than one membrane is employed, the membranes have sequentially smaller pore sizes, depending on the desired size for the finished vesicle. It is to be understood, however, that extrusion could be effected through a single membrane having the requisite pore size.

The vesicles which are employed in the present invention may be prepared from a wide variety of materials, preferably lipids. When the vesicle includes a lipid, it is often referred to as a liposome; however, as known in the art, vesicles can be produced from amphiphilic components which are not lipids. As known in the art, liposomes can be prepared from a wide variety of lipids, including phospholipids, glycolipids, steriods, relatively long chain alkyl esters; e.g., alkyl phosphates, fatty acid esters, e.g. lecithin, fatty amines and the like. A mixture of fatty materials may be employed such as a combination of neutral steriod, a charge amphiphile and a phospholipid. As illustrative examples of phospholipids, there may be mentioned lecithin, sphingomyelin, dipalmitoyl lecithin, and the like. As representative steriods, there may be mentioned cholesterol, cholestanol, lanosterol, and the like. As representative examples of charged amphiphilic compounds, which generally contain from 12 to 30 carbon atomes, there may be mentioned mono-or dialkyl phosphate ester or an alkylamine; e.g., dicetyl phosphate, stearyl amine, hexadecyl amine, dilauryl phosphate, and the like.

The "empty" vesicle may be prepared by any one of a wide variety of procedures. Thus, for example, the empty liposome may be prepared by a reverse emulsion technique, as hereinabove described, except that the liquid does not contain material to be encapsulated. As representative examples of other procedures, there may be mentioned production of multilamellar vesicles by preparation of a vesicle in water containing an electrolyte. As a further example, there may be mentioned a procedure in which a mixture of materials for forming a vesicle and a detergent are dialyzed through a suitable membrane to produce vesicles.

In accordance with a preferred procedure, the "empty" vesicle is produced in a manner such that there is formed large unilamellar vesicles. In accordance with such a preferred procedure, the materials for forming the vesicle are spread as a thin, dry layer, which is brought into contact with a "swelling buffer", which is formed from distilled water or an aqueous solution of low ionic strength (the water is either free of an electrolyte, or if there is any electrolyte, such electrolyte is present in only a small amount). For example, in such a procedure, the "swelling buffer" may be comprised of distilled water containing 2.7% (w/v) glycerol, 1 mM EDTA, at pH 6.7, at 60° C. After agitating the buffer with the dry lipids for about 3 minutes, the "empty" vesicles are formed, and the suspension is cooled on ice. Such a procedure is described, for example by Reeves, et al. in the *Journal of Cell Physiology*, Vol. 73, pages 49–60, 1969.

The size of the final vesicle, including the encapsulated material, as well as the material which is encapsulated into the vesicle is dependent upon the final use for the vesicle. In general, the vesicle, after extrusion, which contains the encapsulated material, has a size of no greater than 1 micron. In most cases, the size is in the order from 0.1 micron to 0.5 micron.

The material which is encapsulated into the vesicle may be a detectable marker, and such detectable markers are of particular use when the vesicle is to be employed for forming a tracer for use in an assay.

Thus, for example, as known in the art, in an assay for an analyte (ligand to be measured) there have been used as detectable markers; radioactive materials, enzymes, chromogens, including both fluorescent dyes and absorbing dyes, chemiluminescent substances, spin labels, etc., and such detectable markers may be incorporated into the vesicle in accordance with the present invention.

The vesicle including the detectable marker may be employed for producing a tracer for use in an assay for an analyte. The ligand which is employed in combination with the vesicle containing a detectable marker is dependent upon the analyte to be assayed. Techniques for labeling a ligand with a vesicle prepared in accordance with the present invention are generally known in the art, and such techniques include adsorption, covalent coupling, derivatization, coactivation, etc.

In one such procedure, the vesicle may be prepared from a component which has been derivatized with the ligand to be employed in the tracer, whereby the "empty" vesicle, when produced is sensitized with the ligand. In accordance with the procedure of the present invention, the derivatized "empty" vesicle is "filled" with a detectable marker. For example, the derivatized "empty" sac is suspended in a liquid containing the detectable marker, and the vesicle suspended in the liquid is extruded through a membrane so as to encapsulate marker.

Alternatively, as known in the art, the vesicle containing a detectable marker, which is prepared in accordance with the invention, may be sensitized with the ligand to be employed in the tracer.

The ligand which is employed in producing a tracer in accordance with the present invention wherein the ligand is labeled with a vesicle including a detectable marker, prepared as hereinabove described, in dependent on the analyte which is to be assayed. Thus, for example, if the assay is a competitive assay, for determining an antigen or hapten, the ligand employed in producing the tracer would be either the analyte or appropriate analog thereof. (The term "appropriate analog" means that the analog of the analyte is bound by the binder for the analyte).

If the assay is a "sandwich" type of assay, then the ligand employed in producing the tracer would be a ligand which is specific for the analyte to be assayed; for example, an antibody elicited in response to the antibody or antigen, to be assayed.

Thus, as should be apparent, the ligand which is employed for producing the tracer may be either an antigen, a hapten or an antibody.

The binder which is used in the assay is also dependent upon the analyte. Thus, for example, if the analyte is an antigen or hapten, the binder may be an antibody or a naturally occurring substance which is specific for the analyte. If the analyte is an antibody, the binder may be either an antibody, an antibody, an antigen or naturally occurring substance which is specific for the analyte.

The binder which is used in the assay may be employed in supported or unsupported form. If supported, the binder may be supported on a wide variety of materials which are generally known to be suitable as supports for a binder in an assay. As representative examples of such materials, there may be mentioned polymers, glass particles, bacterial cells, etc. The solid support may be in a wide variety of forms, including sheet form, particulate form, tube form, as a card or test strip, etc.

The vesicle including a detectable marker may also be used in an assay for an analyte without derivatizing the vesicle; for example, the vesicle may be used as a substance for releasing marker, without being derivatized for binding to a binder for the analyte of the assay.

Thus, in accordance with another aspect of the present invention, there is provided an assay for an analyte in a sample which employs a binder and tracer wherein the binder binds at least the analyte, and the tracer is bound by one of the analyte and binder to provide in the assay a free tracer fraction. In the assay, a vesicle including a detectable marker and which is repaired in accordance with the present invention, is the source of the detectable marker in the assay. in accordance with a preferred procedure, the tracer used in the assay is formed from a ligand which is coupled or conjugated to a vesicle containing the detectable marker, which vesicle containing the detectable marker is produced in accordance with the claimed invention.

In accordance with a representative assay, analyte and tracer compete with a binder specific for both the analyte and tracer. The tracer is the analyte or appropriate analog thereof coupled to a vesicle including a detectable marker; in particular, a chromogen (such as sulforhodamine). The tracer and analyte compete for a limited number of binding sites on the binder, and the amount of tracer which is bound to the binder is inversely proportional to the amount of analyte in the sample. As a result, there is formed in the assay a bound tracer fraction and a free tracer fraction.

After separation of the bound and free tracer fraction, the marker may be released from either the bound or free tracer fraction by lysing the vesicle by procedures known in the art. The amount of marker which is released may then be measured as a measure of the analyte in the sample.

In accordance with a further aspect of the present invention, there is provided an improved tracer for use in an assay wherein the tracer is comprised of a ligand coupled to a vesicle containing a detectable marker which is prepared by the procedure of the present invention (encapsulating marker into a preformed "empty" vesicle). The tracers produced in accordance with the present invention have improved stability. Such improved stability is evidenced by reduced leakage of detectable marker from the interior of the vesicle during storage and/or a reduction in the amount of ligand which becomes uncoupled for the vesicles.

In accordance with still a further aspect of the present invention, there is provided a vesicle having a material encapsulated therein, wherein such vesicle having a material encapsulated therein is prepared in accordance with the present invention. Although the production of such vesicle has been previously described with respect to encapsulating a detectable marker within the vesicle, it is to be understood that materials other than the detectable markers may be encapsulated into the vesicle. Thus, for example, as known in the art, vesicles are suitable for encapsulating biologically active materials, such as a therapeutic agent or drug. As known in the art, such vesicles may be employed in vivo for delivery of a therapeutic agent to tissues. As representative examples of the materials which may be encapsulated into a vesicle in accordance with the present invention, there may be mentioned therapeutic agents such as enzymes, anti-parasitic drugs, anti-cancer drugs, metal chelators, DNA, RNA, macrophage activators, and many other biologically active materials, as well as marker, such as radioisotopes, fluorescent materials and radioopaque compounds, which can be used in vivo for therapeutic and diagnostic purposes. Nutrients for animals or plants, herbicides, and insecticides may also be encapsulated.

The invention will be further described with respect to the following examples, however the scope of the invention is not to be limited thereby:

EXAMPLE 132 umoles chlolesterol, 113 umoles distearolyphosphatidylcholine, 13.2 umoles distearoylphosphatidylglycerol, and 200 ugram distearoylophosphatidylethnolaminedigoxigenin conjugate were dissolved in 20 ml chloroform-methanol (9:1 v/v). The mixture was dried in a 250 ml size round bottom flask using a rotary evaporator at 37° C. The dried lipid film was further dried in-vaccuo at 25° C. for 16 hours and swollen in 2.7% (w/v) glycerol solution containing 1 mM EDTA and 0.02% $NaN_3$ at pH 6.7. Swelling was achieved by gentle swirling at 60° C. for 3 minutes. The turbid liposome suspension was spun for 10 minutes at 2000 rpm to sediment large multilamellar vesicles, and the supernatent was collected and spun for 30 minutes at 30,000 rpm to sediment the large unilamellar vesicle. Loading the vesicles with dye was achieved by resuspending the empty liposome pellet in 20 ml of 0.1M solution of sulforhodamine-B at pH 6.7 and extruding the suspension sequentially through polycarbonate membranes of 1.0 u, 0.4 u, and 0.2 u pore sizes. Thirty ml of buffer containing 20 mM Tris, 20 mM EDTA, 2% (w/v) glycerol, 0.05% DMSO, and 0.02% $NaN_3$ were added, and the liposomes, were spun for 30 minutes at 30,000 rpm. The pellet was resuspended and washed twice in the same buffer to remove unencapsulated dye, and the washed loaded liposomes were diluted in the same buffer at 1 unmole phospholipid phosphorous per ml.

The effectiveness of the liposomes as nonisotopic tracers in immunoassay for digoxin was tested by coating polypropylene 12×75 mm tubes with 1:2000 dilution of sheep anti-digoxin antiserum. The tubes were filled with 50 ul of the liposomes, 100 ul serum containing known amounts of digoxin as clinical samples, and 850 ul of Trissaline buffer at pH 8.0 that also contained 0.1% bovine serum albumin, 1 mM EDTA, and 0.02% sodium azide. After 30 minutes incubation at 37° C., the tubes were emptied by aspiration and washed with Trissaline buffer, 1 ml of 5% Triton X-100 was added to lyse the liposome bounds to the tube wall, and the absorbance was measured by 565 nm on a spectrometer. Absorbance at zero nanograms digoxin was 0.080 O.D., and the standard curve generated for digoxin was linear on a logit-log plot with 50% displacement of liposome binding at the dose of 2 ng digoxin per ml in serum.

Clinical samples gave levels that correlated well with the levels determined by radio-immunoassay.

The present invention is particularly advantageous in that it permits production of improved vesicles. In particular, applicant has found that the vesicles have improved stability. In particular, there is reduced leakage of encapsulated material from the vesicle during the storage and/or less loss of ligand when the vesicle is derivatized with a ligand. For example, the vesicles have been tested at 85° C. for 24 hours, and such vesicles remained stable.

Moreover, the production of the vesicles is better controlled in that the vesicles may be initially produced in an aqueous solution, which is free or essentially free of electrolytes in that it is no longer necessary to include the material to be encapsulated in the vesicle in the solution used for forming the vesicle.

By separating the liposome production process into two independent steps, better control can be achieved over the overall manufacturing procedure. Moreover, such a result is achieved without the necessity of subjecting both the liposome component and encapsulated material to identical treatment.

These and other advantages should be apparent to those skilled in the art from the teachings herein.

Numerous modifications and variations of the present invention are possible in light of the above teachings and, therefore, within the scope of the appended claims, the invention may be practiced otherwise than as particularly described.

What is claimed is:

1. A process for producing a liposome containing an encapsulated material comprising:
   placing a liposome formed before the encapsulation process into a liquid containing the material to be encapsulated, said liposome being essentially free of material to be encapsulated, and temporarily disrupting the liposome while in said liquid to introduce at least a portion of the liquid into the liposome to encapsulate the material in the liposome, said temporary disruption being effected at a temperature of at least 4° C.

2. The process of claim 1 wherein said material is a detectable marker.

3. The process of claim 2 wherein the detectable marker is a chromogen.

4. The process of claim 1 wherein said liposome is perturbed by subjecting the liposome to shear stress.

5. The process of claim 1 wherein the porous material has a pore size of from 0.05 micron to 20 microns.

6. The process of claim 5 wherein said porous material has a pore size from 0.1 micron to 5 microns.

7. The process of claim 1 wherein the lipsome is unilamellar.

8. The process of claim 1 wherein the empty liposome is prepared by swelling dry lipids in an aqueous material of low ionic strength.

9. The process of claim 1 wherein the material is biologically active.

10. The process of claim 1 wherein the material is an enzyme.

11. A process for producing a liposome containing an encapsulated material comprising:
    placing a liposome formed before the encapsulation process into a liquid containing the material to be encapsulated, said liposome being essentially free of material to be encapsulated, and temporarily disrupting the liposome while in said liquid by passing the liposome, while said liposome is in said liquid through a porous material to introduce at least a portion of the liquid into the liposome to encapsulate material in the liposome, said temporary disruption being effected at a temperature of at least 4° C.

12. The process of claim 11 wherein said material is a detectable marker.

13. The process of claim 12 wherein the detectable marker is a chromogen.

14. The process of claim 11 wherein said porous material has a pore size of from 0.05 micron to 10 microns.

15. The process of claim 14 wherein said porous material has a pore size from 0.1 micron to 5 microns.

16. The process of claim 11 wherein said liposome is unilamellar.

17. The process of claim 11 wherein the empty liposome is prepared by swelling dry lipids in an aqueous material of low electrolytic concentration.

18. The process of claim 11 wherein the material is biologically active.

19. The process of claim 11 wherein the material is an enzyme.

* * * * *